United States Patent [19]

Mylari et al.

[11] Patent Number: 5,624,929

[45] Date of Patent: Apr. 29, 1997

[54] PYRROLOQUINOLINE AND PYRROLOPHENOTHIAZINE CARBOXAMIDES AND RELATED COMPOUNDS

[75] Inventors: Banavara L. Mylari, Waterford; Joseph G. Lombardino, Niantic; James M. McManus, Old Lyme, all of Conn.

[73] Assignee: Pfizer Inc., New York, N.Y.

[21] Appl. No.: 445,629

[22] Filed: May 22, 1995

Related U.S. Application Data

[62] Division of Ser. No. 357,615, Dec. 14, 1994, abandoned, which is a division of Ser. No. 438,469, Nov. 13, 1989, Pat. No. 5,403,839.

[51] Int. Cl.$^6$ .................... A61K 31/435; C07D 401/12
[52] U.S. Cl. .................... 514/256; 514/275; 514/339; 514/284; 514/294; 544/333; 546/72; 546/94; 546/96
[58] Field of Search .................... 514/256, 294, 514/284, 275, 339; 544/333; 546/72, 94, 96

[56] References Cited

PUBLICATIONS

Mylari et al, Chemical Abstracts, vol. 113, entry 164927 (1990).
Mylari et al, Chemical Abstracts, vol. 112, entry 118796 (1990).

*Primary Examiner*—John M. Ford
*Attorney, Agent, or Firm*—Peter C. Richardson; Gezina Holtrust; B. Timothy Creagan

[57] ABSTRACT

Compounds of the formula

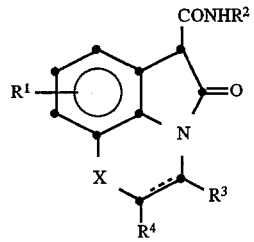

wherein the broken line represents an optional double bond; X is O, S, $CH_2$ or $CH_2CH_2$; $R^1$ is selected from the group consisting of hydrogen, halogen, $C_1$–$C_6$ alkoxy, $C_1$–$C_6$ alkanoyl, $C_1$–$C_6$ alkyl, and $C_1$–$C_6$ alkyl substituted with 1, 2 or 3 halogen atoms; $R^2$ is selected from the group consisting of phenyl, substituted phenyl, heterocyclic groups, and substituted heterocyclic groups, said substituted phenyl and substituted heterocyclic groups being substituted with 1 or 2 substituents independently selected from the group consisting of $C_1$–$C_6$ alkyl, trifuluoromethyl, and halogen; $R^3$ and $R^4$ are independently selected from the group consisting of hydrogen, halogen, $C_1$–$C_6$ alkyl, or trifluoromethyl, or $R^3$ and $R^4$, taken together with the carbon atoms to which they are attached, form a six-membered carbocyclic aromatic ring, said aromatic ring being optionally substituted with one or two substituents selected from the group consisting of halogen, $C_1$–$C_6$ alkyl, and $C_1$–$C_6$ alkyl substituted with 1, 2 or 3 halogen atoms; and the pharmaceutically acceptable salts thereof. The compounds are useful in treating inflammation or other prostaglandin or leukotriene mediated diseases.

10 Claims, No Drawings

PYRROLOQUINOLINE AND PYRROLOPHENOTHIAZINE CARBOXAMIDES AND RELATED COMPOUNDS

This is a division, of application Ser. No. 08/357,615, filed on Dec. 14, 1994, now abandoned, which was a division of application Ser. No. 07/438,469 filed on Nov. 13, 1989, now U.S. Pat. No. 5,403,839, which in turn, is the National Phase of PCT/US88/00781, filed Mar. 11, 1988.

BACKGROUND OF THE INVENTION

The present invention relates to pyrroloquinoline and pyrrolophenothiazine carboxamides and related compounds, methods of preparing such compounds, pharmaceutical compositions comprising such compounds and the use of such compounds in treating inflammation (e.g., arthritis) or other prostaglandin or leukotriene mediated diseases.

Oxindole-carboxamides useful as antiinflammatory agents and analgesics are referred to in U.S. Pat. Nos. 4,556,672, 4,569,942, 4,644,005, 4,678,802, and 4,686,224, and in U.S. Ser. No. 670,697, filed Nov. 13, 1984, and U.S. Ser. No. 821,296, filed Jan. 22, 1986.

U.S. Pat. No. 4,695,571 refers to tricyclic oxidoles as antiinflammatory agents.

U.S. Pat. No. 4,690,943 refers to 1,3-diacyl-2-oxindoles as antiinflammatory agents and analgesics.

U.S. Pat. No. 4,658,037 and U.S. Ser. No. 670,697, filed Nov. 13, 1984, refer to intermediates for preparing oxindole carboxamides.

SUMMARY OF THE INVENTION

The present invention relates to compounds of the formula

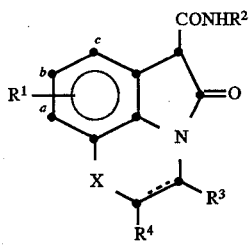

wherein the broken line represents an optional double bond; X is O, S, $CH_2$ or $CH_2CH_2$; $R^1$ is selected from the group consisting of hydrogen, halogen (e.g., fluorine, chlorine, bromine and iodine), $C_1$–$C_6$ alkoxy (e.g., $OCH_3$), $C_1$–$C_6$ alkanoyl, $C_1$–$C_6$ alkyl, and trifluoromethyl; $R^2$ is selected from the group consisting of phenyl, substituted phenyl, heterocyclic groups, and substituted heterocyclic groups, said substituted phenyl and substituted heterocyclic groups being substituted with 1 or 2 substituents independently selected from the group consisting of $C_1$–$C_6$ alkyl, trifluoromethyl, and halogen (e.g. fluorine, chlorine, bromine and iodine); $R^3$ and $R^4$ are independently selected from the group consisting of hydrogen, halogen (e.g., fluorine, chlorine, bromine and iodine), $C_1$–$C_6$ alkyl, and trifluoromethyl, or $R^3$ and $R^4$, taken together with the carbon atoms to which they are attached, form a six-membered carbocyclic aromatic ring, said aromatic ring being optionally substituted with one or two substituents selected from the group consisting of halogen (e.g., fluorine, chlorine, bromine or iodine), $C_1$–$C_6$ alkyl, and trifluoromethyl; and the pharmaceutically acceptable salts thereof. The "floating bond" in formula I is intended to indicate that $R^1$ may be connected to any one of positions a, b and c of the aromatic ring. Position b is preferred. When $R^2$ is a heterocyclic group, $R^2$ is preferably selected from benzothiazole, isoxazole, isothiazole, oxazole, pyridine, thiazole and thiadiazole. The foregoing heterocyclic groups may be substituted as described above.

The present invention also relates to a pharmaceutical composition useful in the treatment of inflammation or other prostaglandin or leukotriene mediated diseases comprising an amount of a compound of the formula I effective to treat inflammation or another prostaglandin or leukotriene mediated disease and a pharmaceutically acceptable carrier.

The present invention also relates to a method of treating a prostaglandin or leukotriene mediated disease comprising administering to a patient in need of such treatment a compound of formula I in an amount effective to treat such disease.

The present invention also relates to intermediates useful in preparing the foregoing compounds and to methods of preparing the foregoing compounds.

A preferred embodiment of the present invention relates to compounds of the formula

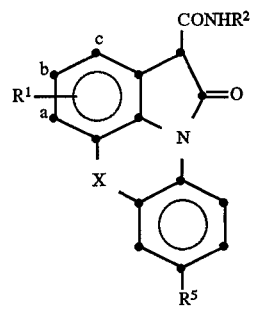

wherein $R^1$, $R^2$ and X are as defined above and $R^5$ is selected from the group consisting of hydrogen, halogen, $C_1$–$C_6$ alkyl, and trifluoromethyl, and the pharmaceutically acceptable salts thereof. More preferably $R^1$ is hydrogen or fluorine; $R^2$ is phenyl, 2,4-difluorophenyl, pyridinyl, thiazolyl, benzothiazolyl, isothiazolyl, or isoxazolyl, or isoxazolyl, and $R^5$ is hydrogen or fluorine.

Another preferred embodiment of the present invention relates to compounds of the formula

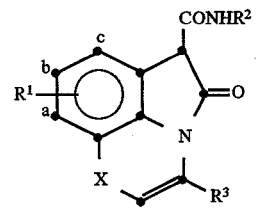

wherein $R^1$, $R^2$, $R^3$ and X are as defined above, and the pharmaceutically acceptable salts thereof. More preferably, $R^1$ is hydrogen, fluoro, or trifluoromethyl; $R^2$ is phenyl, 2,4-difluorophenyl, pyridyl, thiazolyl, isothiazolyl, benzothiazolyl or isoxazolyl; $R^3$ is hydrogen, fluoro, or trifluoromethyl; and X is O, S or $CH_2$.

Another preferred embodiment of the present invention relates to compounds of the formula

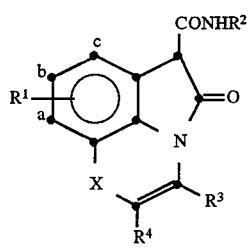

wherein $R^1$, $R^2$, $R^3$, $R^4$ and X are as defined above, with the proviso that $R^3$ and $R^4$ do not form a carbocyclic aromatic ring, and the pharmaceutically acceptable acid addition salts thereof. More preferably, $R^1$ is hydrogen and X is S. Most preferably, $R^1$ is hydrogen, $R^3$ is trifluoromethyl, $R^4$ is fluorine and X is S.

In each of the foregoing preferred embodiments, it is more preferred that $R^1$ be connected to position b of the aromatic ring.

Specific preferred compounds of the present invention include the following:

1,2-dihydro-N-phenyl-1-oxopyrrolo[3,2,1-kl]phenothiazine-2-carboxamide;

1,2-dihydro-N-(2,4-difluorophenyl)-1-oxopyrrolo[3,2,1-kl]phenothiazine-2-carboxamide;

1,2-dihydro-N-(2-pyridyl)-1-oxopyrrolo[3,2,1-kl]phenothiazine-2-carboxamide;

1,2-dihydro-N-[2-thiazolyl]-1-oxopyrrolo[3,2,1-kl]phenothiazine-2-carboxamide;

1,2-dihydro-N-phenyl-1-oxopyrrolo[3,2,1-kl]phenoxazine-2-carboxamide;

1,2-dihydro-N-(2-pyridyl)-1-oxopyrrolo[3,2,1-kl]phenoxazine-2-carboxamide;

N-(2-thiazolyl)-6H-pyrrolo[3,2,1-de]acridin-1(2H)-one-2-carboxamide;

N-(5-methyl-thiazolyl-2)-6H-pyrrido[3,2,1-de]acridin-1(2H)-one-2-carboxamide;

N-(thiazolyl-2)-4-fluoro-6H-pyrrido[3,2,1-de]acridin-1(2H)-one-2-carboxamide;

5-oxo-N-(2-thiazolyl)pyrrolo[1,2,3-de]-tetrahydro-1,4-benzothiazine-6-carboxamide;

2-oxo-N-(2-thiazolyl)-8-fluoro-4H-pyrrolo[3,2,1-ij]quinoline-1-carboxamide; and 5,6-dihydro-2-fluoro-5-oxo-N-(2-thiazolyl)-3-trifluoromethylpyrrolo[1,2,3-de]-1,4-benzothiazine-6-carboxamide.

Preferred compositions of the present invention include the foregoing preferred and specific preferred compounds.

DETAILED DESCRIPTION OF THE INVENTION

The compounds of the present invention may be prepared as described in the following reaction scheme:

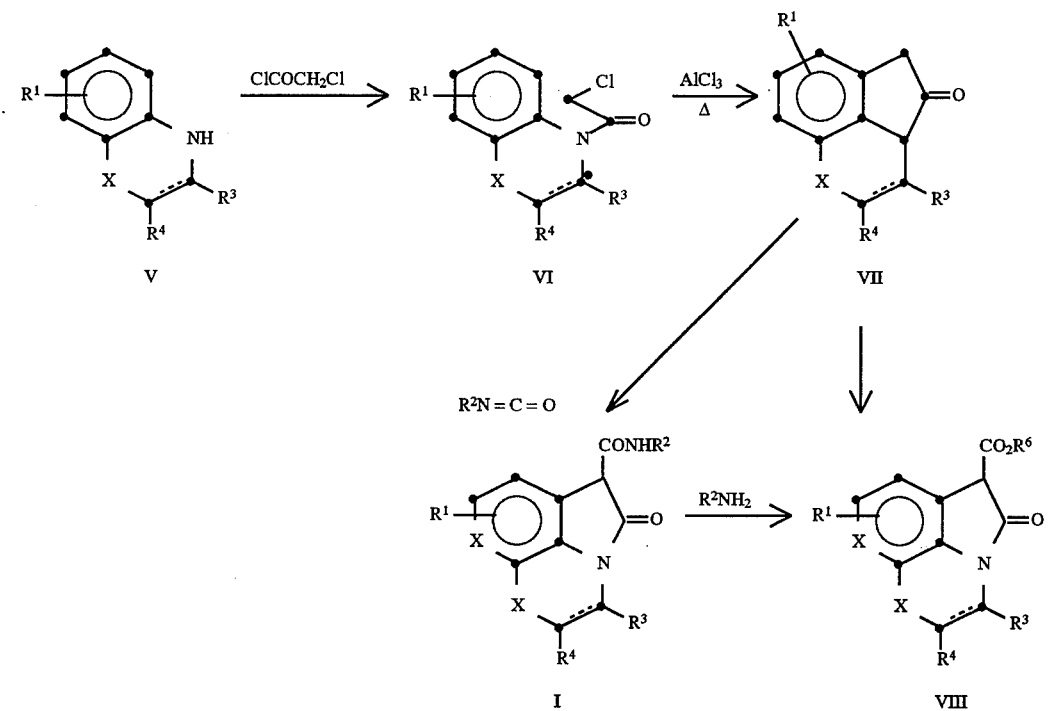

In the foregoing reaction scheme, $R^1$, $R^2$, $R^3$ and $R^4$ are as defined above.

The compound of the formula V is reacted in an inert solvent with $ClCOCH_2Cl$ to provide the compound of formula VI. Either or both chlorine atoms in the compound of formula VI may be replaced by a bromine atom. The solvent is preferably an aromatic hydrocarbon such as benzene or toluene or a halohydrocarbon such as methylene chloride or chloroform. The temperature is not critical and generally ranges from about 20° C. to about 120° C. Preferably, the temperature is the reflux temperature of the solvent.

The compound of the formula VII is generally obtained by fusion of the compound of formula VI with anhydrous $AlCl_3$ at a temperature within a few degrees of the melting point of the compound of formula VI, using a temperature no greater than about 200° C.

The compound of the formula VII is reacted in an alcoholic solvent, preferably a $C_1$–$C_4$ alcohol, or an aprotic polar solvent (e.g., dimethylformamide (DMF)) with a base such as sodium hydride, sodium $C_1$–$C_4$ alkoxide or potassium $C_1$–$C_4$ alkoxide and with dialkylcarbonate or alkylchloroformate wherein the alkyl groups may contain 1 to 4 carbon atoms, preferably 1 or 2 carbon atoms, to provide the compound of formula VIII wherein $R^6$ is $C_1$–$C_4$ alkyl. The temperature is not critical and generally ranges from about 0° C. to about 100° C. Preferably, the temperature is the reflux temperature of the solvent.

In order to prepare a compound of the formula I, the compound of the formula VII is reacted in an inert solvent in the presence of a base such as sodium hydride or potassium hydride with a compound of the formula $R^2N=C=O$ wherein $R^2$ is as defined above. The solvent is preferably DMF or diglyme. The temperature is not critical and generally ranges from about 0° C. to about 30° C. The temperature is preferably room temperature (about 22° C.).

The compound of the formula I may also be prepared by reacting a compound of the formula VIII, wherein $R^6$ is as defined above, with a compound of the formula $R^2NH_2$ in an inert solvent. The colvent is preferably toluene or xylene. The temperature is not critical and generally ranges from about 100° C. to about 200° C. The temperature is preferably the reflux temperature of the solvent.

The pressure used in each of the foregoing reactions is not critical. Generally, a pressure of about 0.5 to about 2 atmospheres, preferably ambient pressure (about one atmosphere) will be used.

Salts of compounds of the formula I may be prepared in a conventional manner by reacting a compound of the formula I with an appropriate base, for example, an inorganic base such as an alkali metal hydroxide or an alkaline earth metal hydroxide.

The activity of the compounds of formula I in the treatment of pulmonary, asthmatic, allergic and inflammatory diseases may be determined by a standard test measuring an agent's ability to inhibit cyclooxygenase and 5-lypoxygenase enzyme activity of rat basophil leukemia (RBL-1)cells. According to this test as described by Jakschick et al., *Prostaglandins*, 16, 733–747 (1978), and Jakschick et al., *Biochem. Biophys. Res. Commun.*, 95, 103–110 (1980), a monolayer of RBL-1 cells is grown for 1 or 2 days in spinner culture in Eagle's minimum essential medium, 15% heat-inactivated fetal calf serum and an antibiotic/antimycotic mixture. The cells are washed after centrifugation and incubated in a buffer. A volume of 0.5 ml of cell suspension is preincubated at 30° C. for ten minutes with a 1 microliter dimethylsulfoxide (DMSO) solution of the agent to be tested. The incubation is initiated by simultaneous addition of 5 microliters ($^{14}C$)— arachidonic acid in ethanol and 2 microliters calcium ionophore (A-21387) in DMSO for final concentrations of 5 and 7.6 micromolar, respectively. Five minutes later, the incubation is terminated by the addition of 0.27 ml acetonitrile/acetic acid (100:3). High pressure liquid chromatography is performed using acetonitrile/water/acetic acid solvent. Radiolabeled prostaglandin $D_2$ ($PGD_2$), leukotrine $B_4$ ($LTB_4$), 5-hydroxyeicosatetraenoic acid (5-HETE), and unreacted arachidonic acid are determined. The inhibitory effect on the cyclooxygenase pathway is assessed from the reduction of $PGD_2$ levels and the inhibitory effect on the 5-lipoxygenase pathway is assessed from the decrease in the amount of $LTB_4$ and 5-HETE.

The compounds of the formula I and their pharmaceutically acceptable salts are effective inhibitors of mammalian leukotriene or prostaglandin biosynthesis or both and are thus useful in the treatment of various leukotriene or prostaglandin mediated conditions. In particular, the compounds have utility, both as the sole active agent and also in combination with other active agents, for the treatment of various pulmonary, gastrointestinal, inflammatory, dermatological and cardiovascular conditions such as inflammation, arthritis, allergy, psoriasis, asthma, bronchitis, pulmonary hypertension and hypoxia, peptic ulcers, inflammatory bowel disease or cardiovascular spasm, such as acute myocardial infarctions, and the like in mammals, especially in humans. The compounds of the formula I and their pharmaceutically acceptable salts are particularly useful in treating arthritis.

For treatment of the various conditions described above, the compounds of formula I and their pharmaceutically acceptable salts may be administered to a subject in need of treatment by a variety of conventional routes of administration, including oral, by injection, topical, rectal, and in an aerosol carrier composition for administration by inhalation.

The exact dosage of a compound of the present invention will depend upon such factors as the age, weight and condition of the patient and the severity of disease. In general, however, a therapeutically effective dose of a compound of formula I or a pharmaceutically acceptable salt thereof will range from 0.1 to 25 mg/kg body weight of the subject to be treated per day, preferably 0.5 to 10 mg/kg per day.

Although the compounds of formula I and their pharmaceutically acceptable salts can be administered alone, they will generally be administered in admixture with a pharmaceutical carrier selected with regard to the intended route of administration and standard pharmaceutical practice. For example, oral administration may be in the form of tablets containing such excipients as starch or lactose, or in the form of elixirs or suspensions containing flavoring or coloring agents. In the case of animals, the compounds of the present invention are advantageously contained in an animal feed or drinking water. For parenteral injection, they may be used in the form of a sterile aqueous solution which may contain other solutes, for example, enough salt or glucose to make the solution isotonic. Other active compounds, including NSAIDS (non-steroidal antiinflammatory drugs) may be administered along with the compounds of the present invention.

The following non-limiting Preparations and Examples are illustrative of the preparation of compounds of the present invention. All melting points referred to in the Preparations and Examples are uncorrected.

PREPARATION OF STARTING MATERIALS

The compounds described in Table I were used in preparing compounds of the present invention. Unless a reference is given, the compounds are commercially available:

TABLE 1

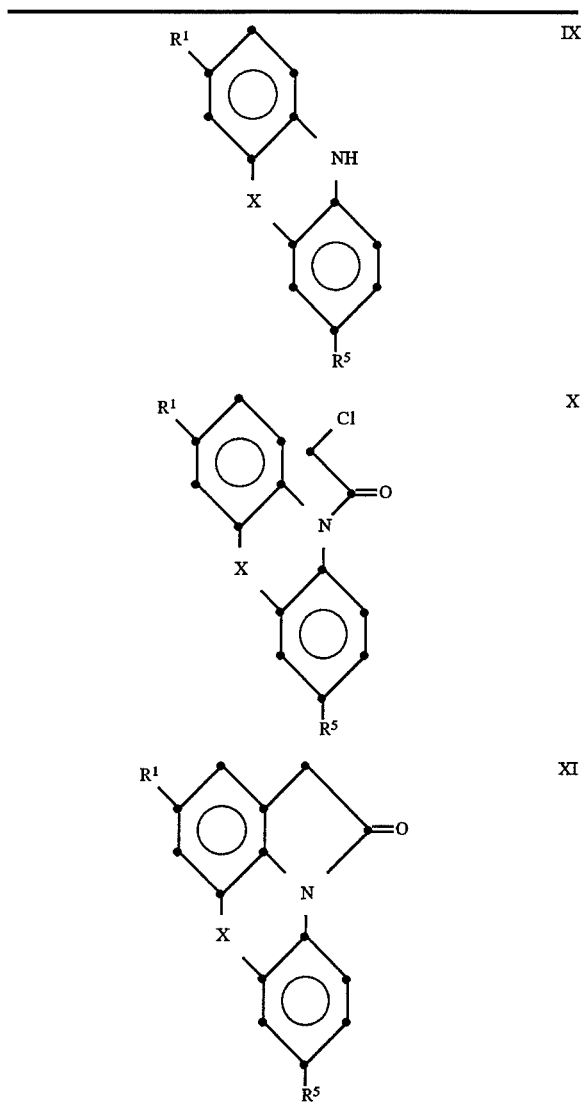

| Compound Number | Formula | X | R¹ | R⁵ | Reference |
|---|---|---|---|---|---|
| P1 | IX | S | H | H | Commercial material |
| P2 | IX | O | H | H | Commercial material |
| P3 | IX | CH$_2$ | H | H | Commercial material |
| P4 | IX | CH$_2$ | H | F | J. Indian Chem. Soc., 38, 877 (1961) |
| P5 | IX | CH$_2$ | F | F | J. Am. Chem. Soc., 63, 1563 (1941) |
| P6 | IX | CH$_2$CH$_2$ | H | H | Commercial material |
| P7 | X | S | H | H | Acad. Sc. Paris, 265, 758 (1967) |
| P8 | X | O | H | H | J. Het. Chem., 6, 809 (1963) |
| P9 | X | CH$_2$CH$_2$ | H | H | British Patent 897,052 |
| P10 | XI | S | H | H | Acad. Sc. Paris, 265, 758 (1967) |
| P11 | XI | CH$_2$CH$_2$ | H | H | British Patent 897,052 |

PREPARATION 1

2-Fluoro-3-trifluoromethyl-N-chloroacetyl-1,4-dihydrobenzothiazine

2-Fluoro-3-trifluoromethyl-1,4-dihydrobenzothiazine prepared as described in *Chemistry Letters*, 167 (1983), was reacted with chloroacetyl chloride to yield the title compound. $^1$H NMR (CDCl$_3$, 60 MHz), ppm ($\delta$): 4.3 (S, 2H), 6.9–7.0 (m, 4H).

Similarly prepared were the following:

2-fluoro-N-chloroacetylacridan (m.p. 121°–124° C.);

2,7-difluoro-N-chloroacetylacridan (m.p. 128°–131° C.);

1,2,3,4-tetrahydro-6-fluoro-N-chloroacetylquinoline [$^1$H NMR(CDCl$_3$, 60 MHz), ppm ($\delta$) 2.0 (m, 2H), 2.7 (m, 2H), 3.7 (m, 2H), 4.2 (s, 2H), 6.7–7.2 (m, 3H)];

2,3-dihydro-3,7-dimethyl-N-chloroacetyl-1,4-benzoxazine and 3,7-dimethyl-N-chloroacetyl-1,2,3,4-tetrahydrobenzoxazine (m.p. 59°–61°).

PREPARATION 2

2-Fluoro-3-trifluoromethylpyrrolo[1,2,3-de]-1,4-benzothiazin-5(6H)-one

A mixture of the title compound of Preparation 1 (3.11 g) and anhydrous aluminum chloride (4.0 g) was heated in an open beaker at 150° C. for 0.5 hours. After evalution of gaseous hydrogen chloride ceased, the residue was cooled to room temperature and then quenched with a mixture of 10 ml concentrated HCl and 200 ml of ice water. The resulting dark brown solid was extracted with ethyl acetate (2×100 ml) and the organic extract was evaporated to dryness. The residue was purified by chromatography over silica gel, using methylene chloride as the eluant, to obtain the title compound as a white crystalline solid, m.p. 128°–130° C.

Similarly prepared were the following:

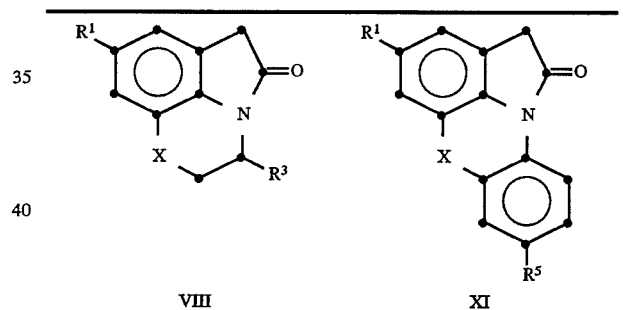

| Compound | Formula | X | R¹ | R³ | R⁵ | Reference or Melting Point °C. |
|---|---|---|---|---|---|---|
| P12 | VIII | S | H | H | — | 85–87 |
| P13 | VIII | CH$_2$ | H | H | — | * |
| P14 | VII | O | H | CH$_3$ | CH$_3$ | 96–98 |
| P15 | VIII | CH$_2$ | F | H | — | 119–121 |
| P16 | IX | O | H | — | H | 182–183 |
| P17 | IX | CH$_2$ | H | — | H | 175–176 |
| P18 | IX | CH$_2$ | H | — | F | 134–138 |
| P19 | IX | CH$_2$ | F | — | F | 206–208 |
| P20 | VIII | CH$_2$ | CH$_3$ | — | — | * |

*British Patent 1,394,373

PREPARATION 3

5,6-Dihydro-2-fluoro-5-oxo-3-trifluoromethylpyrrolo[1,2,3-de]-1,4-benzothiazine-6-carboxylic acid, ethyl ester To a solution of sodium ethoxide prepared from sodium metal (0.35 g) and ethanol (30 ml) was added the title compound of Preparation 2 (1.37 g) followed by diethyl carbonate (1.77 g). The solution was heated at 65° C. for 3 hours. The reaction mixture was cooled, poured into ice water, acidified with dilute HCl to pH about 3 and the resulting solid collected by filtration. $^1$H NMR(CDCl$_3$, 60 MHz), ppm (δ): 1.3 (t, J=8 Hz, 3H), 4.1 (q, J=8 Hz, 2H), 4.3 (s, 1H, 6.9–7.2 (m, 3H).

Similarly, prepared were the following:

ethyl-5,6-dihydro-pyrrolo[1,2,3-de]-tetrahydro-1,4-benzothiazine-5(6H)-one-1-carboxylate [$^1$H NMR (CDCl$_3$, 60 MHz), ppm (δ): 1.3 (t, J=8 Hz, 3H), 3.0 (m, 2H), 3.9–4.2 (m, 5H), 6.9–7.1 (m, 3H)];

ethyl-2-oxo-5,6-dihydro 3,8-dimethyl-pyrrolo[1,2,3-de] tetrahydro-1,4-benzoxazin-5(6)-one-1-carboxylate [$^1$H NMR (CDCl$_3$, 60 MHz), ppm(δ): 1.2 (t, J=8 Hz, 3H), 1.5 (d, J=12 Hz, 3H), 2.4 (s, 3H), 4.1 (m, 3H), 4.2 (m, 2H), 6.8 (m, 2H)];

ethyl-2-oxo-1,2,5,6-tetrahydro-4-H-pyrollo[3,2,1-J] quinoline-1-carboxylate [$^1$HNMR(CDCl$_3$, 60 MHz), ppm (δ): 1.5 (t, J=7 Hz, 3H), 2.1 (m, 2H), 2.9 (m, 2H), 3.9 (t, J=7 Hz, 2H), 4.2 (m, 2H), 7.2 (m, 3H)];

ethyl-2-oxo-7-fluoro-1,2,5,6-tetrahydro-4-H-pyrollo[3,2,1-iJ]quinoline-1-carboxylate (m.p. 118°–120° C.); and ethyl-2-oxo-7-methyl-1,2,5,6-tetrahydro-4-H-pyrollo[3,2,1-iJ]quinoline-1-carboxylate [$^1$HNMR(CDCl$_3$, 60 MHz), ppm (δ): 1.5 (t, J=7 Hz, 3H), 2.0 (m, 2H), 2.4 (s,3H), 2.9 (m, 2H), 3.9 (t, J=7 Hz; 2H), 4.2 (m, 2H), 7.2 (dd, J=2, 2H)].

PREPARATION 4

Methylpyrrolo[3,2,1-kl]phenoxazine-1-one-2-carboxylate

To a slurry of sodium hydride (0.39 g) in 20 ml of DMF (dimethylformamide) was added pyrrolo[3,2,1-kl] phenoxazine (1.4 g), prepared as described according to Preparation 2, and the resulting dark red solution was stirred at room temperature for 0.5 hours. To this solution, was added methyl chloroformate (0.95 g), dropwise, over a period of 10 minutes. The reaction mixture was stirred for 2 hours at room temperature, and it was then poured onto ice water (200 ml). The resulting mixture was then acidified to pH 2.0 with concentrated HCl and the mixture was then extracted with methylene chloride (200 ml). The extract was washed with water, dried and evaporated to dryness to yield the title compound as a solid (0.06 g; m.p. 124°–127° C.).

PREPARATION 5

Ethyl 6H-pyrido[3,2,1-de]acridin-1(2H)-one 10 carboxylate

To a freshly prepared solution of sodium ethoxide in ethanol (from 0.35 g sodium metal and 10 ml ethanol) was added 6H-pyrido[3,2,1-de]acridin-1(2H)-one (1.2 g) portionwise over a period of 10 minutes. To the resulting dark red solution was slowly added diethyl carbonate (1.77 g) and the solution was then refluxed for 3 hours. The reaction mixture was cooled, acidified to pH 2 with concentrated HCl and then extracted with methylene chloride. The organic extract was washed with water and was then collected, dried and evaporated to dryness to obtain a light amber solid (1.8 g; m.p. 113°–118° C.).

PREPARATION 6

Following the method of Preparation 4 or Preparation 5, the following compounds were prepared;

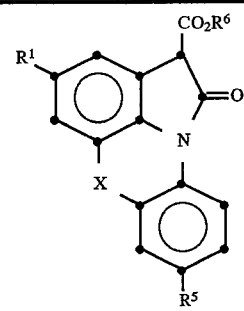

| Compound | X | R$^1$ | R$^5$ | R$^6$ | Melting Point °C. | Method |
|---|---|---|---|---|---|---|
| P21 | S | H | H | CH$_3$ | 144–145 | Preparation 4 |
| P22 | CH$_2$ | H | H | CH$_3$ | 89–92 | Preparation 4 |
| P23 | CH$_2$ | F | F | C$_2$H$_5$ | 134–136 | Preparation 5 |
| P24 | CH$_2$—CH$_2$ | H | H | CH$_3$ | 121–123 | Preparation 4 |

EXAMPLE 1

1,2-Dihydro-N-(2,4-difluorophenyl)-1-oxopyrrolo[3,2,1-kl]phenothiazine-2-carboxamide To a suspension of sodium hydride (0.14 g) in DMF (10 ml) was added pyrrolo[3,2,-1kl]phenothiazine-1-one (0.48 g) and to the resulting solution was slowly added 2,4-difluorophenyl isocyanate (0.31 g). The reaction mixture was stirred for 12 hours and then poured onto ice water (50 ml). The resulting mixture was acidified to pH 2.0 with 6N HCl and the precipitated solid was collected and then air dried to yield the title compound (2.84 g). A sample recrystallized from methylene chloride had a m.p. of 208°–209° C.

EXAMPLE 2

1,2-Dihydro-N-[2-pyridyl]-1-oxopyrrolo[3,2,1-kl] phenothiazine-1-carboxamide

A mixture of methyl pyrrolo[3,2,-1-kl]phenoxazine-1-one-2-carboxylate (0.7 g), 2 aminopyridine (0.28 g) and xylene (20 ml) was heated under reflux for 0.5 hours. It was then cooled to room temperature and the precipitated yellow solid was collected by filtration (0.64 g, m.p. 224°–225° C.).

EXAMPLES 3–5

Starting, in each case, from the corresponding lactam or ester, compounds E1, E2, E11–E14, E18–E21, and E43–E46, described below, were prepared by the method of Example 1 and compounds E3–E10, E15–E17, E22–E42, and E47–E83, described below, were prepared by the method of Example 2.

Example 3

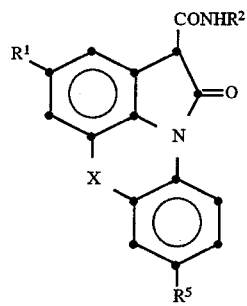

| Compound Number | X | R¹ | R⁵ | R² | Melting Point °C. |
|---|---|---|---|---|---|
| E1 | S | H | H | 4-Cl-phenyl | 247–248 |
| E2 | S | H | H | 2-F,4-F-phenyl | 208–209 |
| E3 | S | H | H | phenyl | 236–239 |
| E4 | S | H | H | 2-pyridyl | 228–229 |
| E5 | S | H | H | 2-thiazolyl | 203–205 |
| E6 | S | H | H | 2-thiazolyl-5-$CH_3$ | 218 |
| E7 | S | H | H | 5-isothiazolyl-3-methyl | 228–231 |
| E8 | S | H | H | 2-F,6-F-phenyl | 237–241 |
| E9 | S | H | H | 2-F,5-F-phenyl | 207–208 |
| E10 | S | H | H | 2[1,3,4-thiazolyl]-5-$CF_3$ | 186–188 |
| E11 | O | H | H | 4-Cl-phenyl | 268–270 |
| E12 | O | H | H | 4-F-phenyl | 254–256 |
| E13 | O | H | H | phenyl | 254 |
| E14 | O | H | H | 2-F,4-F-phenyl | 238–239 |
| E15 | O | H | H | 2-pyridyl | 224–225 |
| E16 | O | H | H | 3-isoxozolyl-5-$CH_3$ | 197–198 |
| E17 | O | H | H | 2-thiazolyl | 206–208 |
| E18 | $CH_2$ | H | H | 4-F-phenyl | 224–226 |
| E19 | $CH_2$ | H | H | 2-F,4-F-phenyl | 186 |
| E20 | $CH_2$ | H | H | phenyl | 209 |
| E21 | $CH_2$ | H | H | 4-Cl-phenyl | 235–237 |
| E22 | $CH_2$ | H | H | 2-thiazolyl | 231–234 |
| E23 | $CH_2$ | H | H | 2-pyridyl | 209 |
| E24 | $CH_2$ | H | H | 2-thiazolyl-5-$CH_3$ | 231–232 |
| E25 | $CH_2$ | H | H | 5-isothiazolyl-3-$CH_3$ | 211–213 (dec.) |
| E26 | $CH_2$ | H | H | 2-F,6-F-phenyl | 264–265 |
| E27 | $CH_2$ | H | H | 2-pyridyl-6-$CH_3$ | 232–233 |
| E28 | $CH_2$ | H | H | 3-isoxozolyl-5-$CH_3$ | 198 (dec.) |
| E29 | $CH_2$ | H | H | 3-1H-pyrazolyl | 248–250 |
| E30 | $CH_2$ | H | H | 2-1H-imidazolyl | 268 (dec.) |
| E31 | $CH_2$ | H | H | 2-pyrimidinyl | 219–221 |
| E32 | $CH_2$ | H | H | 2-(1,2,4-thiadiazolyl)-5-$CF_3$ | 204–205 (dec.) |
| E33 | $CH_2$ | H | F | 5-isothiazolyl-3-$CH_3$ | 203–205 |
| E34 | $CH_2$ | H | F | 2-[1,2,4-thiadiazolyl]-5-phenyl | 211–214 |
| E35 | $CH_2$ | H | F | 2-F,4-F-phenyl | 222–223 |
| E36 | $CH_2$ | H | F | 2-F,5-F-phenyl | 184–186 |
| E37 | $CH_2$ | H | F | 2-thiazolyl | 168–174 (dec.) |
| E38 | $CH_2$ | H | F | 2-[1,3,4-thiadiazolyl] | 208–210 |
| E39 | $CH_2$ | F | F | 2-pyridyl | 246–248 |
| E40 | $CH_2$ | F | F | 2-thiazolyl | 199–200 |
| E41 | $CH_2$ | F | F | 2-thiazolyl-5-$CH_3$ | 223 (dec.) |
| E42 | $CH_2$ | F | F | 5-isothiazolyl-3-$CH_3$ | 233 (dec.) |
| E43 | $CH_2CH_2$ | H | H | 2-F,4-F-phenyl | 217–218 |
| E44 | $CH_2CH_2$ | H | H | 4-Cl-phenyl | 194–196 |
| E45 | $CH_2CH_2$ | H | H | 4-F-phenyl | 224–225 |
| E46 | $CH_2CH_2$ | H | H | phenyl | 224–225 |
| E47 | $CH_2CH_2$ | H | H | 2-pyridyl | 202–204 |
| E48 | $CH_2CH_2$ | H | H | 2-thiazolyl | 248–249 |
| E49 | $CH_2CH_2$ | H | H | 3-methylthioethyl | 158–159 |
| E50 | $CH_2CH_2$ | H | H | 3-isoxazolyl-5-$CH_3$ | 168–169 |
| E51 | $CH_2CH_2$ | H | H | 2-thiazolyl-4$CH_3$—5$CH_3$ | 261–262 |
| E52 | $CH_2CH_2$ | H | H | 2-benzothiazolyl | 167–168 |
| E53 | $CH_2CH_2$ | H | H | 2-thiazolyl-5-$CH_3$ | 234–236 |

Example 4

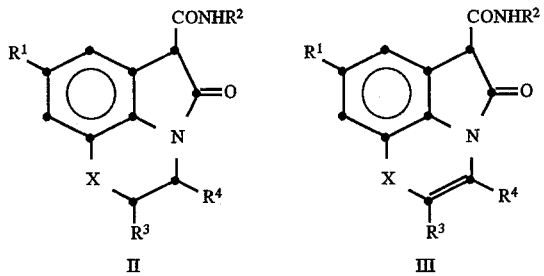

| Compound Number/ Formula | X | $R^1$ | $R^2$ | $R^4$ | $R^3$ | Melting Point °C. |
|---|---|---|---|---|---|---|
| E54/II | O | $CH_3$ | | $CH_3$ | H | 205–206 |
| E55/II | O | $CH_3$ | 2-pyridyl | $CH_3$ | H | 168–169 |
| E56/II | O | $CH_3$ | phenyl | $CH_3$ | H | 190–191 |
| E57/II | O | $CH_3$ | 2F,4F-phenyl | $CH_3$ | H | 181–183 |
| E58/II | O | $CH_3$ | 2-thiazolyl | $CH_3$ | H | 172–174 |
| E59/II | O | $CH_3$ | 2-benzothiazolyl | $CH_3$ | H | 184–185 |
| E60/II | O | $CH_3$ | 2[1,3,4-thiadiazolyl]-5-$CF_3$ | $CF_3$ | H | 186–188 |
| E61/II | O | $CH_3$ | 2-oxazolyl-5-$CH_3$ | $CH_3$ | H | 194–195 |
| E62/II | O | $CH_3$ | 5-isothiazolyl-3-$CH_3$ | $CH_3$ | H | 219–220 |
| E63/III | S | H | 2-thiazolyl | F | $CF_3$ | 211 |
| E64/III | S | H | 2-F,4-F-phenyl | F | $CF_3$ | 214–216 |
| E65/III | S | H | 5-isothiazolyl-3-$CH_3$ | F | $CF_3$ | 240–242 |

EXAMPLE 5

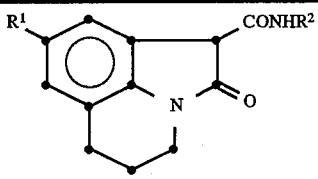

| Compound Number | $R^1$ | $R^2$ | Melting Point °C. |
|---|---|---|---|
| E66 | H | 2-Cl, 4-Cl-phenyl | 199–200 |
| E67 | H | phenyl | 175–176 |
| E68 | H | 2-pyridyl | 246–247 |
| E69 | H | 3-methyl-2-pyridyl | 213–214 |
| E70 | H | 4-F-phenyl | 191–194 |
| E71 | H | 2-thiazolyl | 208–210 |
| E72 | H | | 164–168 |
| E73 | H | 2-Cl, 5-Cl-phenyl | 187–189 |
| E74 | H | 3-Cl, 4-Cl-phenyl | 200–201 |
| E75 | H | 4-Br-phenyl | 206–207 |
| E76 | H | 2-F, 5-F-phenyl | 176–180 |
| E77 | H | 2-F, 4-F-phenyl | 174–175 |
| E78 | H | 4-methyl-2-thiazolyl | 202–205 |
| E79 | H | 4,5-dimethyl-2-thiazolyl | 249–252 |
| E80 | F | 2-thiazolyl | 213–214 (dec.) |
| E81 | $CH_3$ | 2-pyridyl | 189–190 |
| E82 | $CH_3$ | 5-isothiazolyl-3-methyl | 174–177 |
| E83 | $CH_3$ | 2-benzothiazolyl | 178–180 |

EXAMPLE 6

The compounds numbered E1–E83 and the compounds of Examples 1 and 2 were assayed according to the method of Jakschick et al. described above. The compounds were found to have inhibitory activity against cyclooxygenase or 5-lipoxygenase or both.

We claim:
1. A compound of the formula

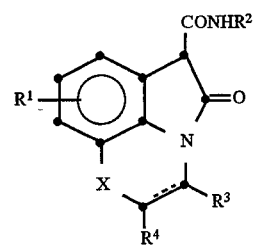

wherein the broken line represents an optional double bond; X is $CH_2$; $R^1$ is selected from the group consisting of hydrogen, halogen, $C_1$–$C_6$ alkoxy, $C_1$–$C_6$ alkanoyl, $C_1$–$C_6$ alkyl, and trifluoromethyl; $R^2$ is selected from the group consisting of phenyl, substituted phenyl, heterocyclic selected from the group consisting of pyridyl, thiazolyl, oxazolyl, isoxazolyl, pyrazolyl, isothiazolyl, pyrimidinyl, thiadizolyl, and benzothiazolyl, and substituted heterocyclic groups, said substituted phenyl and substituted heterocyclic groups being substituted with 1 or 2 substituents independently selected from the group consisting of $C_1$–$C_6$ alkyl, trifluoromethyl, and halogen; $R^3$ and $R^4$ are independently selected from the group consisting of hydrogen, halogen, $C_1$–$C_6$ alkyl, and trifluoromethyl, or $R^3$ and $R^4$ taken together with the carbon atoms to which they are attached form a six-membered carbocyclic aromatic ring, said aromatic ring being optionally substituted with one or two substituents selected from the group consisting of halogen, $C_1$–$C_6$ alkyl, and trifluoromethyl; or a pharmaceutically acceptable salt thereof.

2. A compound according to claim 1, wherein $R^2$ is a heterocyclic group selected from the group consisting of benzothiazole, isoxazole, isothiazole, oxazole, pyridine, thiazole and thiadiazole, said heterocyclic groups being optionally substituted with one or two substituents selected from the group consisting of halogen, $C_1$–$C_6$ alkyl, and trifluoromethyl.

3. A compound according to claim 1, said compound being a compound of the formula

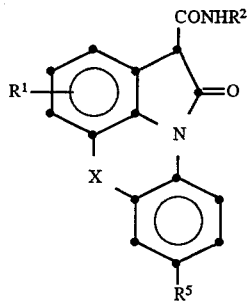

wherein $R^1$, $R^2$ and X are as defined above and $R^5$ is selected from the group consisting of hydrogen, halogen, $C_1$–$C_6$ alkyl, and trifluoromethyl, or a pharmaceutically acceptable salt thereof.

4. A compound according to claim 3, wherein $R^1$ is hydrogen or fluorine; $R^2$ is phenyl, 2,4-difluorophenyl, pyridinyl, thiazolyl, benzothiazolyl, isothiazolyl, or isoxazolyl, and $R^5$ is hydrogen or fluorine.

5. A compound according to claim 1, said compound being a compound of the formula

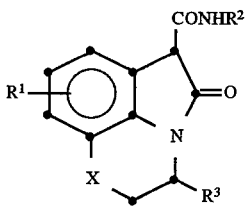

wherein $R^1$, $R^2$, $R^3$ and X are as defined above, or a pharmaceutically acceptable salt thereof.

6. A compound according to claim 5, wherein $R^1$ is hydrogen, fluoro, or trifluoromethyl; $R^2$ is phenyl, 2,4-difluorophenyl, pyridyl, thiazolyl, isothiazolyl, benzothiazolyl or isoxazolyl; $R^3$ is hydrogen, fluoro, or trifluoromethyl; and X is $CH_2$.

7. A compound according to claim 1, said compound being a compound of the formula

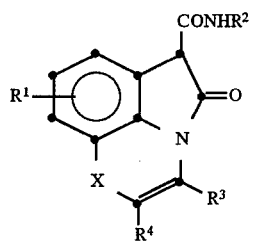

wherein $R^1$, $R^2$, $R^3$, $R^4$ and X are as defined above, with the proviso that $R^3$ and $R^4$ do not form a carbocyclic aromatic ring, or a pharmaceutically acceptable acid addition salt thereof.

8. A compound according to claim 1, said compound being selected from the group consisting of N-(2-thiazolyl)-6H-pyrrolo[3,2,1-de]acridin-1(2H)-one-2-carboxamide;

N-(5-methyl-thiazolyl-2)-6H-pyrrido[3,2,1-de]-acridin-1(2H)-one-2-carboxamide;

N-(thiazolyl-2)-4-fluoro-6H-pyrrido[3,2,1-de]-acridin-1(2H)-one-2-carboxamide;

2-oxo-N-(2-thiazolyl)-8-fluoro-4H-pyrrolo[3,2,1-ij]quinoline-1-carboxamide; and the pharmaceutically acceptable salts thereof.

9. A pharmaceutical composition for the treatment of pulmonary, asthmatic, allergic and inflammatory diseases in a mammal, including a human, comprising an amount of a compound of claim 1 or a pharmaceutically acceptable salt thereof, effective in such treatments and pharmaceutically acceptable carrier.

10. A method for the treatment of pulmonary, asthmatic, allergic and inflammatory diseases in a mammal, including a human, comprising administering to said mammal an amount of a compound of claim 1 or a pharmaceutically acceptable salt thereof, effective in treating such a condition.

* * * * *